United States Patent
Ahn et al.

(10) Patent No.: US 10,693,179 B2
(45) Date of Patent: Jun. 23, 2020

(54) ELECTROLYTE SOLUTION FOR LITHIUM SECONDARY BATTERY AND LITHIUM SECONDARY BATTERY COMPRISING THE SAME

(71) Applicant: LG Chem, Ltd., Seoul (KR)

(72) Inventors: Kyoung Ho Ahn, Daejeon (KR); Chul Haeng Lee, Daejeon (KR); Yi Jin Jung, Daejeon (KR); Jung Hoon Lee, Daejeon (KR)

(73) Assignee: LG Chem, Ltd. (KR)

( * ) Notice: Subject to any disclaimer, the term of this patent is extended or adjusted under 35 U.S.C. 154(b) by 167 days.

(21) Appl. No.: 15/750,707

(22) PCT Filed: Aug. 19, 2016

(86) PCT No.: PCT/KR2016/009183
§ 371 (c)(1),
(2) Date: Feb. 6, 2018

(87) PCT Pub. No.: WO2017/030416
PCT Pub. Date: Feb. 23, 2017

(65) Prior Publication Data
US 2019/0006703 A1 Jan. 3, 2019

(30) Foreign Application Priority Data

Aug. 19, 2015 (KR) .................. 10-2015-0116637
Aug. 18, 2016 (KR) .................. 10-2016-0104607

(51) Int. Cl.
*H01M 10/0525* (2010.01)
*H01M 10/0568* (2010.01)
(Continued)

(52) U.S. Cl.
CPC ....... *H01M 10/0525* (2013.01); *C07C 309/72* (2013.01); *H01M 10/0567* (2013.01);
(Continued)

(58) Field of Classification Search
CPC ..... H01M 2300/0025; H01M 10/0525; H01M 10/0567; H01M 2300/0028; H01M 10/0569; H01M 10/0568; C07C 309/72
(Continued)

(56) References Cited

U.S. PATENT DOCUMENTS

2002/0197537 A1  12/2002  Kim et al.
2007/0059588 A1   3/2007  Lee et al.
(Continued)

FOREIGN PATENT DOCUMENTS

CN    101533929 A    9/2009
EP    1553654 A2    7/2005
(Continued)

OTHER PUBLICATIONS

English language machine translation of JP2014146558 (A)—Aug. 14, 2014 "Nonaqueous electrolyte, and nonaqueous electrolyte battery using same" by Fukamizu Koji et al. (Year: 2014).*

(Continued)

*Primary Examiner* — Jonathan G Jelsma
*Assistant Examiner* — Omar M Kekia
(74) *Attorney, Agent, or Firm* — Lerner, David, Littenberg, Krumholz & Mentlik, LLP (57) ABSTRACT

The present invention relates to an electrolyte solution for a lithium secondary battery that includes an additive for forming a stable SEI film and a protective layer on a surface of an electrode to prevent a chemical reaction between the electrolyte solution and the electrode, and a lithium secondary battery having improved life characteristics and high-temperature stability by including the same.

11 Claims, 2 Drawing Sheets

(51) Int. Cl.
*H01M 10/0567* (2010.01)
*C07C 309/72* (2006.01)
*H01M 10/0569* (2010.01)

(52) U.S. Cl.
CPC ... *H01M 10/0568* (2013.01); *H01M 10/0569* (2013.01); *H01M 2300/0025* (2013.01); *H01M 2300/0028* (2013.01)

(58) Field of Classification Search
USPC .................................................... 429/231.95
See application file for complete search history.

(56) References Cited

U.S. PATENT DOCUMENTS

| | | | |
|---|---|---|---|
| 2009/0280414 | A1 | 11/2009 | Koh et al. |
| 2014/0030610 | A1* | 1/2014 | Abe ................. H01G 11/58 429/330 |
| 2014/0212770 | A1 | 7/2014 | Abe et al. |
| 2017/0294682 | A1 | 10/2017 | Ahn et al. |

FOREIGN PATENT DOCUMENTS

| | | | | |
|---|---|---|---|---|
| EP | 3203568 | A1 | 8/2017 | |
| JP | 2009245923 | A | 10/2009 | |
| JP | 2014146558 | A * | 8/2014 | ........... Y02E 60/122 |
| JP | 2017536652 | A | 12/2017 | |
| KR | 20020086069 | A | 11/2002 | |
| KR | 20070031807 | A | 3/2007 | |
| KR | 100746479 | B1 | 8/2007 | |
| KR | 100867535 | B1 | 11/2008 | |
| KR | 20080097599 | A | 11/2008 | |
| KR | 20140063672 | A | 5/2014 | |
| WO | 2016053040 | A1 | 4/2016 | |

OTHER PUBLICATIONS

Search report from International Application No. PCT/KR2016/009183, dated Nov. 28, 2016.
Extended European Search Report for Application No. EP16837358.7 dated Mar. 14, 2018.

* cited by examiner

ELECTROLYTE SOLUTION FOR LITHIUM SECONDARY BATTERY AND LITHIUM SECONDARY BATTERY COMPRISING THE SAME

CROSS-REFERENCE TO RELATED APPLICATION

The present application is a national phase entry under 35 U.S.C. § 371 of International Application No. PCT/KR2016/009183, filed Aug. 19, 2016 which claims priority from Korean Patent Application No. 10-2015-0116637, filed on Aug. 19, 2015 and Korean Patent Application No. 10-2016-0104607, filed on Aug. 18, 2016, the disclosures of which are incorporated herein by reference.

TECHNICAL FIELD

The present invention relates to an electrolyte solution for a lithium secondary battery capable of securing cycle life characteristics and high-temperature durability and a lithium secondary battery comprising the same.

BACKGROUND ART

The use of portable electronic devices is increasing nowadays as downsizing and weight-lightening of electronic equipment are possible due to development of the high-tech electronic industry, and the need for a battery having high energy density as a power source of such portable electronic devices is increasing.

A battery is a device for converting chemical energy that is generated during an electrochemical oxidation reduction reaction of a chemical substance in the battery into electrical energy, and can be classified as a primary battery that needs to be discarded when energy inside the battery is used up and a secondary battery that is rechargeable several times.

The secondary battery has an advantage of being able to be used by being charged and discharged several times using reversible interconversion between chemical energy and electrical energy. Particularly, because a lithium secondary battery has advantages of being rechargeable, having energy density per unit weight that is three times or more higher compared to an existing lead storage battery, nickel-cadmium battery, nickel-hydride battery, nickel-zinc battery, and the like, and being quickly chargeable, the lithium secondary battery is used in various ways as a driving power source of a portable electronic device such as a video camera, a cellphone, and a laptop computer.

The lithium secondary battery is used by injecting an electrolyte solution into a battery cell that includes a positive electrode including a positive electrode active material capable of intercalating and deintercalating lithium ions and a negative electrode including a negative electrode active material capable of intercalating and deintercalating lithium ions.

Because the lithium secondary battery is operated at a high driving voltage, a non-aqueous organic solvent in which a lithium salt is dissolved is used instead of an aqueous electrolyte that has high reactivity with lithium. The organic solvent is preferably stable at high voltage, has high ion conductivity and a high dielectric constant, and has low viscosity.

For example, when a carbonate-based polar non-aqueous solvent is used in the lithium secondary battery, an irreversible reaction in which an excessive amount of charge is used occurs due to a side reaction between a negative electrode/a positive electrode and an electrolyte solution during initial charging. Due to the irreversible reaction, a passivation layer such as a solid electrolyte interface (SEI) (hereinafter referred to as an "SEI film") is formed at a negative electrode surface, and a protective layer is formed at a positive electrode surface.

The SEI film and the protective layer prevent decomposition of an electrolyte solution during charging and discharging and serve as an ion tunnel. Consequently, a life of a lithium secondary battery can be improved as the SEI film and the protective layer have higher stability and lower resistance.

Thus, to improve battery performance, the need for an organic electrolyte solution capable of forming an SEI film and a protective layer which have excellent stability and low resistance is coming to the fore.

PRIOR ART DOCUMENT

Korean Patent Application Laid-Open Publication No. 10-2007-0031807

DISCLOSURE

Technical Problem

To solve the above-described problem, the present invention provides an electrolyte solution for a lithium secondary battery that comprises an electrolyte additive capable of improving battery performance.

Further, the present invention provides a lithium secondary battery that comprises the electrolyte solution for a lithium secondary battery.

Technical Solution

According to an embodiment of the present invention, an electrolyte solution for a lithium secondary battery that includes an electrolyte salt and an organic solvent, the electrolyte solution further including a compound represented by Chemical Formula 1 below as an electrolyte additive, is provided.

[Chemical Formula 1]

In the above formula, R is a linear or branched alkylene group with a carbon number of 1 to 3, $R_1$ is a linear or branched alkylene group with a carbon number of 1 to 5 or an arylene group with a carbon number of 5 to 8, and n is an integer of 0 to 10.

The compound represented by Chemical Formula 1 may be included by an amount of 0.05 wt % to 7 wt % based on the total weight of the electrolyte solution.

Further, according to an embodiment of the present invention, a lithium secondary battery that includes a positive electrode, a negative electrode, a separator interposed between the positive electrode and the negative electrode, and the electrolyte solution for a lithium secondary battery of the present invention is provided.

Advantageous Effects

According to the present invention, an electrolyte solution for a lithium secondary battery that includes an additive for forming a more stable SEI film and a protective layer on a surface of an electrode to prevent a chemical reaction between the electrolyte solution and the electrode is provided so that a lithium secondary battery having improved life characteristics and high-temperature stability can be fabricated.

DESCRIPTION OF DRAWINGS

Because the following drawings attached to the present specification illustrate exemplary embodiments of the present invention and serve to facilitate understanding of the technical idea of the present invention together with the above-described content of the invention, the present invention should not be limitedly interpreted on the basis of the drawings.

BEST MODE

Hereinafter, the present invention will be described in detail. Here, concepts of terms or words used in the present specification and claims are properly defined by the inventor to give description in the best way to assist understanding of the invention, and the scope of the invention should not be interpreted as limited to the scope of the description below.

Before describing the present invention, in the present specification, in "carbon number a to b," "a" and "b" refer to the number of carbon atoms in a specific functional group. That is, the functional group may include "a" to "b" carbon atoms. For example, "linear or branched alkylene group with a carbon number of 1 to 3" refers to an alkyl group with a carbon number of 1 to 3 that includes 1 to 3 carbon atoms, i.e., —$CH_2$—, —$CH_2CH_2$—, —$CH_2CH_2CH_2$—, —$CH_2CH$($CH_3$)—, and —$CH(CH_3)CH_2$—.

In the present specification, the term "alkyl group" or "alkylene group" refers to an aliphatic hydrocarbon group that is branched or not branched. The alkyl group or alkylene group may be substituted or unsubstituted. In one example, the alkylene group includes a methylene group, an ethylene group, a propylene group, an isopropylene group, a butylene group, an isobutylene group, a tert-butylene group, a pentylene group, a 3-pentylene group, a hexylene group, a cyclopropylene group, a cyclopentylene group, a cyclohyxylene group, a cycloheptylene group, and the like but is not limited thereto, and each of them may be selectively substituted in another example.

In the present specification, the term "aryl group" or "arylene group" refers to an aromatic ring or an aromatic ring system (i.e., a ring that shares an adjacent pair of atoms) that includes only carbon in the ring structure. When aryl is a ring system, all rings in the system are aromatic. In one example, the arylene group is a phenylene group, a biphenylene group, a naphthylene group, a phenanthrenylene group, a naphthacenylene group, and the like, but is not limited thereto. The aryl group may be substituted or unsubstituted in another example.

The lithium secondary battery known to date has had difficulty in preventing the corrosion of metallic materials and is insufficient for maintaining the performance at an effective level especially under extreme conditions such as overcharge, overdischarge and high-temperature preservation. Accordingly, the present invention provides an electrolyte solution for a lithium secondary battery that includes an additive for forming an SEI film and a protective layer on a surface of an electrode to prevent a chemical reaction between the electrolyte solution and the electrode so that a lithium secondary battery having improved life characteristics and high-temperature stability can be fabricated.

Hereinafter, examples of the present invention will be described in detail.

Non-Aqueous Electrolyte Solution for Secondary Battery

Specifically, according to an embodiment of the present invention, an electrolyte solution for a lithium secondary battery that includes an electrolyte salt and an organic solvent and further includes a compound represented by Chemical Formula 1 below as an electrolyte additive is provided.

[Chemical Formula 1]

In the above formula, R is a linear or branched alkylene group with a carbon number of 1 to 3, $R_1$ is a linear or branched alkylene group with a carbon number of 1 to 5 or arylene group with a carbon number of 5 to 8, and n is an integer of 0 to 10.

More specifically, R is a linear alkylene group with a carbon number of 1 to 3, $R_1$ is an arylene group with a carbon number of 5 to 8, and n is an integer of 0 to 5.

When the electrolyte solution of the present invention includes a compound that contains a sulfonate group as a substituent such as the compound represented by Chemical Formula 1 above, as an electrolyte additive, a stable film is formed on a surface of an electrode due to a coordinate bond between the sulfonate group and metal of an electrode, and corrosion of the electrode, particularly, a surface of a positive electrode, can be prevented. That is, when a surface of an electrode of the lithium secondary battery is exposed to the electrolyte solution under extreme conditions such as overcharge, overdischarge and high-temperature preservation, because water molecules are eliminated as the sulfonate group of the compound included as the electrolyte additive reacts with a hydroxyl group at the surface of the electrode as in Reaction Formula 1 below, and a film is formed on the surface of the electrode as oxygen of the sulfonate group forms a coordinate bond with a positive charge site of a metal component on surface of the electrode, a chemical reaction between the electrolyte solution and the electrode can be suppressed.

[Reaction Formula 1]

When the compound that contains an unsaturated functional group or a polar functional group such as a tri$_{(in\ battery)}$ used at an end as the electrolyte additive, because an electron is more easily received from a negative electrode compared to a polar solvent, reduction at a lower voltage may occur before a polar solvent is reduced. That is, the unsaturated functional group or the polar functional group contained in the compound represented by Chemical Formula 1 may be more easily reduced and/or decomposed into radicals and/or ions during charging. The radicals and/or ions may precipitate or form an insoluble compound by bonding with a lithium ion, and the insoluble compound may react with various functional groups present on a surface of a carbon-based negative electrode or with the carbon-based negative electrode itself and form a covalent bond or be adsorbed onto the negative electrode surface. As a result, due to such bond and/or adsorption, a modified SEI film having improved stability so that a firm state can be maintained even after a long period of charging and discharging is formed at the negative electrode surface. Because the firm modified SEI film can effectively reduce or prevent penetration of an electrolyte solution, gas that is generated during high-temperature storage can be decreased.

A compound that contains an isocyanate group or a nitrile group as a substituent, such as the compound represented by Chemical Formula 1 above, may be easily oxidized and/or decomposed into radicals and/or ions during charging compared to a polar solvent. Consequently, when a compound containing the isocyanate group or nitrile group as a substituent is included as the electrolyte additive of the present invention, a modified protective film that consists of a complex may be formed on the surface of the electrode by reacting with various transition metal ions or a hydroxyl group present on the surface of the electrode as in Reaction Formula 2 below. The film formed by the complex may maintain a firm state for a long period even at high temperature storage and after charging and discharging compared to a film (a protective layer) formed only by decomposition of an organic solvent and secure stability.

[Reaction Formula 2]

-continued

The firm modified protective layer may more effectively prevent entry of an organic solvent, in which a lithium ion is solvated, into the electrode during intercalation of the lithium ion. Consequently, because the modified protective film more effectively prevents direct contact between the organic solvent and a positive electrode, reversibility of adsorption/release of the lithium ion is further improved, and thus, high-temperature stability of a battery can be improved.

As a result, by including the compound represented by Chemical Formula 1 above containing both the sulfonate group and the isocyanate group (—NCO) and a triple bond structure as the electrolyte additive, the electrolyte solution for a secondary battery of the present invention respectively forms a stable SEI film and a protective film on surfaces of a positive electrode and a negative electrode, thereby considerably improving high-temperature life characteristics, high-temperature durability, and the like of a lithium secondary battery even under extreme conditions such as high-temperature preservation.

Specifically, the compound represented by Chemical Formula 1 above may be represented by Chemical Formula 1a or Chemical Formula 1b below.

[Chemical Formula 1a]

[Chemical Formula 1b]

Here, the compound represented by Chemical Formula 1 may be included in an amount of 0.05 wt % to 7 wt %, preferably, 0.1 wt % to 5 wt % based on a total weight of the non-aqueous electrolyte solution. When the amount of the additive is less than 0.05 wt %, a problem in that capacity is degenerated as the storage period is longer due to an insufficient effect of forming an SEI film and a protective film at electrode surfaces may occur. Also, when the amount of the additive is greater than 7 wt %, a problem in that a thickness of a battery increases as the storage period is longer due to an insufficient effect of suppressing gas generation as a result of a side reaction and the like occurs.

In the electrolyte solution of the present invention, the electrolyte salt may consist of a combination of (i) a positive ion selected from the group consisting of $Li^+$, $Na^+$, and $K^+$ and (ii) a negative ion selected from the group consisting of $PF_6^-$, $BF_4^-$, $Cl^-$, $Br^-$, $I^-$, $ClO_4^-$, $AsF_6^-$, $B_{10}Cl_{10}^-$, $CH_3CO_2^-$, $CF_3SO_3^-$, $SbF_6^-$, $AlCl_4^-$, $AlO_4^-$, $CH_3SO_3^-$, $N(CF_3SO_2)_2$ and $C(CF_2SO_2)_3$, may typically include a single substance or a mixture of two or more substances selected from the group consisting of LiCl, LiBr, LiI, $LiClO_4$, $LiBF_4$, $LiB_{10}Cl_{10}$, $LiPF_6$, $LiCF_3SO_3$, $LiCH_3CO_2$, $LiCF_3CO_2$, $LiAsF_6$, $LiSbF_6$, $LiAlCl_4$, $LiAlO_4$, $LiCH_3SO_3$, chloroborane lithium, lower aliphatic lithium carbonates, and lithium tetraphenylborate, and other than the above, an electrolyte salt such as a lithium imide salt including lithium bisperfluoroethanesulfonimide ($LiN(C_2F_5SO_2)_2$, LiBETI), lithium fluoromethanesulfonimide (LiFSI), or lithium (bis)trifluoromethanesulfonimide, ($LiN(CF_3SO_2)_2$, LiTFSI) typically used in an electrolyte solution for a lithium secondary battery may be used without limitation. Specifically, the electrolyte salt may include a single substance or a mixture of two or more substances selected from the group consisting of $LiPF_6$, $LiCH_3CO_2$, $LiCF_3CO_2$, $LiCH_3SO_3$, LiFSI, LiTFSI and $(CF_3SO_2)_2NLi$.

Although the electrolyte salt may be appropriately changed within a generally usable range, the electrolyte salt may be included in the electrolyte solution in a concentration of 0.8 M to 1.5 M to obtain the optimal effect of forming an anti-corrosive film on a surface of an electrode. If the concentration of the electrolyte salt exceeds 1.5 M, it is difficult to realize an effect of forming a stable film.

Also, in the non-aqueous electrolyte solution of the present invention, the non-aqueous organic solvent may include common organic solvents that may be used as a non-aqueous organic solvent of a lithium secondary battery, such as a cyclic carbonate solvent, a linear carbonate solvent, an ester solvent, and a ketone solvent, and the solvents may be used solely, or two or more types thereof may be mixed in an appropriate ratio to be used.

The cyclic carbonate solvent may be any one or a mixed solution of two or more selected from the group consisting of ethylene carbonate (EC), propylene carbonate (PC), and butylene carbonate (BC). Also, the linear carbonate solvent may be any one or a mixed solution of two or more selected from the group consisting of dimethyl carbonate (DMC), diethyl carbonate (DEC), dipropyl carbonate (DPC), ethyl methyl carbonate (EMC), vinylene carbonate (VC), fluoroethylene carbonate (FEC), methyl propyl carbonate (MPC), and ethyl propyl carbonate (EPC). Also, the ester solvent may be any one or a mixed solution of two or more selected from the group consisting of methyl acetate, ethyl acetate, propyl acetate, methyl propionate, ethyl propionate, γ-butyrolactone, γ-valerolactone, γ-caprolactone, δ-valerolactone, and ε-caprolactone. Also, as the ketone solvent, polymethyl vinyl ketone or the like may be used.

Secondary Battery

In the present invention, with respect to a lithium secondary battery that includes a positive electrode, a negative electrode, a separator interposed between the positive electrode and the negative electrode, and an electrolyte solution, a lithium secondary battery that contains the electrolyte solution for a lithium secondary battery of the present invention as the electrolyte solution is provided.

The positive electrode may be formed by applying a positive electrode active material on an electrode (positive) current collector. Here, the positive electrode current collector is not particularly limited as long as it has high conductivity and does not cause a chemical change in the battery, and for example, stainless steel, aluminum, nickel, titanium, sintered carbon, or aluminum or stainless steel whose surface is coated treated with carbon, nickel, titanium, silver, or the like may be used as the positive electrode current collector. Here, to increase an adhesive force with the positive electrode active material, various forms such as a film, a sheet, a foil, a net, a porous body, a foam, a nonwoven fabric, or the like having fine irregularities formed on its surface may be used for the positive electrode current collector.

Also, the positive electrode active material is not particularly limited as long as it is a lithium-containing transition metal oxide used as a positive electrode active material when a general lithium secondary battery is fabricated. For example, the positive electrode active material may be any one or a mixture of two or more selected from the group consisting of $LiCoO_2$, $Li_xNiO_2(0.5<x<1.3)$, $Li_xMnO_2$ $(0.5<x<1.3)$, $Li_xMn_2O_4(0.5<x<1.3)$, $Li_x(Ni_aCo_bMn_c)O_2$ $(0.5<x<1.3, 0<a<1, 0<b<1, 0<c<1, a+b+c=1, NCM)$, $Li_xNi_{1-y}Co_yO_2(0.5<x<1.3, 0<y<1)$, $Li_xCo_{1-y}Mn_yO_2(0.5<x<1.3, 0\leq y<1)$, $Li_xNi_{1-y}Mn_yO_2(0.5<x<1.3, 0\leq y<1)$, $Li_x(Ni_aCo_bMn_c)O_4(0.5<x<1.3, 0<a<2, 0<b<2, 0<c<2, a+b+c=2)$, $Li_xMn_{2-z}Ni_zO_4(0.5<x<1.3, 0<z<2)$, $Li_xMn_{2-z}Co_zO_4$ $(0.5<x<1.3, 0<z<2)$, $Li_xCoPO_4(0.5<x<1.3)$ and $Li_xFePO_4$ $(0.5<x<1.3)$. As a specific example, $Li_x(Ni_aCo_bMn_c)O_2$ $(0.5<x<1.3, 0<a<1, 0<b<1, 0<c<1, a+b+c=1, NCM)$, that is, any one selected from the group consisting of $Li(Ni_{1/3}Mn_{1/3}Co_{1/3})O_2$, $Li(Ni_{0.6}Mn_{0.2}Co_{0.2})O_2$, $Li(Ni_{0.5}Mn_{0.3}Co_{0.2})O_2$ and $Li(Ni_{0.8}Mn_{0.1}Co_{0.1})O_2$ or two or more lithium transition metal oxides therefrom may be the positive electrode active material.

The negative electrode may be formed by applying a negative electrode active material on a negative electrode current collector. Here, the negative electrode current collector is not particularly limited as long as it has conductivity and does not cause a chemical change in the battery, and for example, copper, stainless steel, aluminum, nickel, titanium, sintered carbon, or copper or stainless steel whose surface is coated treated with carbon, nickel, titanium, silver, or the like, an aluminum-cadmium alloy, and the like may be used as the positive electrode current collector. Like the positive electrode current collector, various forms such as a film, a sheet, a foil, a net, a porous body, a foam, a nonwoven fabric, or the like having fine irregularities formed on its surface may be used for the negative electrode current collector.

Also, a carbon material, lithium metal, silicon, tin, or the like onto or from which a lithium ion can be adsorbed or released during fabrication of a general lithium secondary battery may be used for the negative electrode active material, and for example, all of low crystalline carbon, high crystalline carbon, and the like may be used as the carbon material. Soft carbon and hard carbon are typical examples of the low crystalline carbon, and natural graphite, Kish graphite, pyrolytic carbon, mesophase pitch based carbon fiber, meso-carbon microbeads, mesophase pitches, high-temperature sintered carbon such as petroleum or coal tar pitch derived coke are examples of the high crystalline carbon.

The positive and negative electrode active materials may further include a binder and a conductive material.

Here, the binder is a component for assisting the bonding between the conductive material, the active material, and the current collector, and is commonly added in an amount of 1 wt % to 50 wt % based on the total weight of the electrode mixture. Examples of the binder include polyvinylidene fluoride (PVDF), polyvinyl alcohol, carboxymethylcellulose (CMC), starch, hydroxypropylcellulose, regenerated cellulose, polyvinylpyrrolidone, tetrafluoroethylene, polyethylene, polypropylene, ethylene-propylene-diene polymers (EPDM), sulfonated-EPDM, styrene-butadiene rubber, fluorine rubber and various copolymers thereof.

The conductive material is a component for further improving the conductivity of the electrode active material, and may be added in an amount of 1 wt % to 20 wt % based on the total weight of the electrode mixture. The conductive material is not particularly limited as long as it has conductivity and does not cause a chemical change in the battery, and for example, graphite such as natural graphite and artificial graphite; carbon black such as acetylene black, Ketjenblack, channel black, furnace black, lamp black, and thermal black; conductive fibers such as carbon fiber and metal fiber; metal powder such as carbon fluoride, aluminum, and nickel powder; conductive whiskey such as zinc oxide and potassium titanate; a conductive metal oxide such as titanium oxide; and conductive materials such as polyphenylene derivatives may be used as the conductive material.

In the present invention, a battery formation process can be performed after a battery assembly that includes a positive electrode, a negative electrode, and a separator interposed between the positive electrode and the negative electrode is mounted in a battery case, and then an electrolyte solution containing the additive for preventing electrode corrosion of the present invention is injected and impregnated. Also, by performing an aging process at room temperature or at a high temperature before and after activation, efficiency of a urethane reaction between the —NCO group, which is an end group of the compound represented by Chemical Formula 1 above, and OH, which is an impurity on the surface of the electrode, is further increased, and the protective effect is expected to increase further.

Here, because a passivation film is formed on the surface of the electrode as the electrolyte solution and the surface of the electrode react with each other, and the electrode corrosion phenomenon can be prevented by preventing exposure of the surface of the electrode even under extreme conditions such as overcharge, overdischarge, and high-temperature preservation, overall performance such as cycle life characteristics of a lithium secondary battery can be improved.

Specific examples have been described in the above detailed description of the present invention. However, various modifications are possible without departing from the scope of the present invention. The technical idea of the present invention should not be limitedly defined to the above-described examples of the present invention but should be defined by the claims below and their equivalents.

MODE FOR CARRYING OUT THE INVENTION

Examples

Example 1

(Fabrication of Negative Electrode)

After mixing 98% by weight of natural graphite, 1.0% by weight of a styrene-butadiene rubber (SBR) binder (ZEON), and 1.0% by weight of carboxymethylcellulose (CMC, NIPPON A&L), the mixture was injected into distilled water and was stirred for 60 minutes using a mechanical stirrer, thereby fabricating a negative electrode active material slurry. The slurry was applied in a thickness of about 60 μm on a copper current collector having a thickness of 10 μm using a doctor blade, was dried in a hot air drier at 100° C. for 0.5 hour, was dried again under a vacuum condition at 120° C. for 4 hours, and was roll-pressed to fabricate a negative electrode plate.

(Fabrication of Positive Electrode)

After mixing 97.45% by weight of $Li(Ni_{0.6}Mn_{2.0}Co_{0.2})O_2$, 0.5% by weight of artificial graphite (SFG6, Timcal) powder, 0.7% by weight of carbon black (Ketjenblack, ECP), 0.25% by weight of modified acrylonitrile rubber (BM-720H, Zeon Corporation), and 1.1% by weight of polyvinylidene fluoride (PVdF, 56020, Solvay), the mixture was injected into an N-methyl-2-pyrrolidone solvent and then stirred using a mechanical stirrer for 30 minutes, thereby fabricating a positive electrode active material slurry. The slurry was applied in a thickness of about 60 μm on an aluminum current collector having a thickness of 20 μm using a doctor blade, was dried in a hot air drier at 100° C. for 0.5 hour, was dried again under a vacuum condition at 120° C. for 4 hours, and was roll-pressed to fabricate a positive electrode plate.

(Preparation of Electrolyte Solution)

An organic electrolyte solution was prepared by adding 0.2% by weight of the compound represented by Chemical Formula 1a above as an additive to a non-aqueous solvent (ethylene carbonate (EC), ethyl methyl carbonate (EMC) and diethyl carbonate (DEC)=3:5:2 vol %) that contains 1.0M $LiPF_6$.

(Fabrication of Secondary Battery)

An electrode assembly was fabricated by interposing a separator, which is made of porous polyethylene having a thickness of 14 μm and coated with a ceramic, between the negative electrode and the negative electrode fabricated above, the electrode assembly was placed inside a case, and a lithium secondary battery was fabricated by injecting the prepared electrolyte solution into the case.

Example 2

An electrolyte solution and a lithium secondary battery including the same were prepared using the same method as in Example 1, except that 3% by weight of the compound of Chemical Formula 1b was included as an electrolyte additive instead of the compound of Chemical Formula 1a.

Comparative Example 1

An electrolyte solution and a lithium secondary battery including the same were prepared using the same method as in Example 1, except that an electrolyte additive was not included.

Comparative Example 2

An electrolyte solution and a lithium secondary battery including the same were prepared using the same method as in Example 1, except that 0.02% by weight of the compound of Chemical Formula 1a was included as the electrolyte additive.

Comparative Example 3

An electrolyte solution and a lithium secondary battery were prepared using the same method as in Example 1, except that 7.3% by weight of the compound of Chemical Formula 1a was included as the electrolyte additive.

Experimental Examples

Experimental Example 1: Capacity Decrease Measurement with Respect to High-Temperature Storage (60° C.)

The lithium secondary batteries fabricated in Examples 1 and 2 and Comparative Examples 1 to 3 were charged to state-of-charge (SOC) 100% at 25° C. and stored in a chamber at 60° C. Then, capacity deterioration behaviors depending on the storage period were measured, and the results thereof are shown in FIG. 1.

Figure 1:
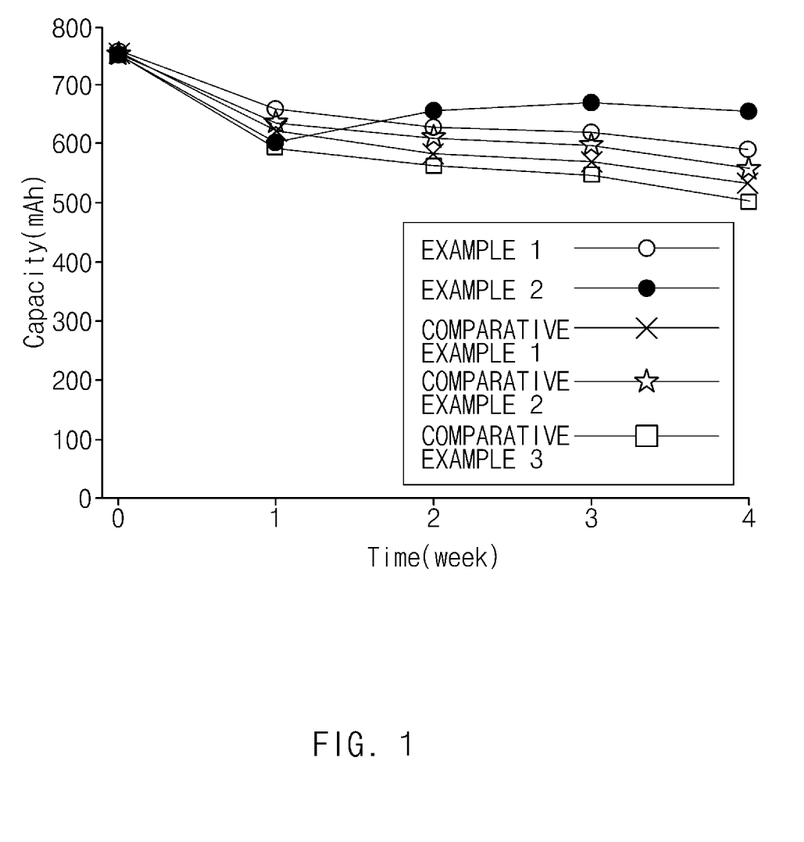
FIG. 1 is a graph showing high-temperature (60° C.) storage capacity retention rate results of a lithium secondary battery according to Experimental Example 1 of the present invention.

Referring to FIG. 1, it can be recognized that the capacity deterioration rates depending on the storage period of the secondary batteries of Examples 1 and 2 are lower compared to those of the secondary batteries of Comparative Examples 1 to 3.

Experimental Example 2: Gas Generation Measurement at High Temperature (60° C.)

The lithium secondary batteries fabricated in Examples 1 and 2 and Comparative Examples 1 to 3 were charged to SOC 100% at 25° C. and stored in a chamber at 60° C. Then, cell thickness changes due to gas generation depending on the storage period were measured, and the results thereof are shown in FIG. 2.

Figure 2:
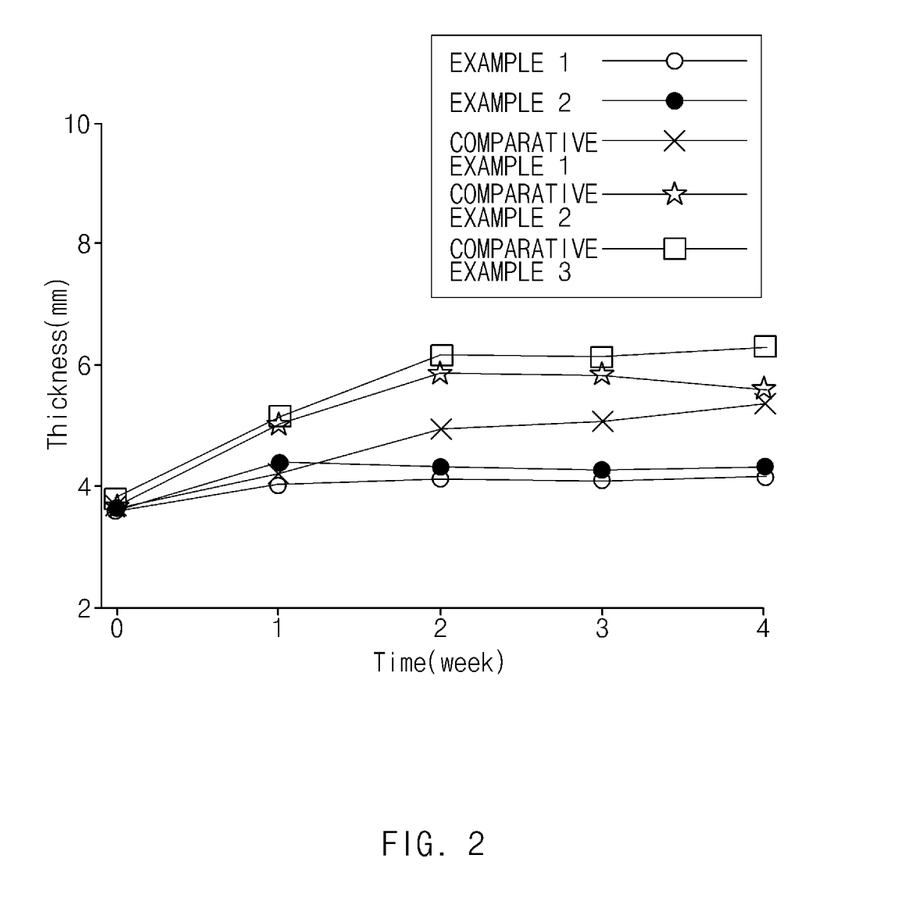
FIG. 2 is a graph showing thickness change results of a cell during the high-temperature (60° C.) storage of the lithium secondary battery according to Experimental Example 1 of the present invention.

Referring to FIG. 2, it can be recognized that the increase (change) in cell thickness depending on the storage period of the secondary batteries of Examples 1 and 2 is lower compared to that of the secondary batteries of Comparative Examples 1 to 3.

From the results obtained from Experimental Examples 1 and 2, it can be confirmed that, because the secondary batteries of Examples 1 and 2 form a stable film on a surface of an electrode by an electrolyte additive, the secondary batteries can effectively reduce or prevent penetration of an electrolyte solution, and consequently, an effect of decreasing gas generation due to a side reaction of the electrolyte solution during high-temperature storage can be realized.

The invention claimed is:

1. An electrolyte solution for a lithium secondary battery comprising an electrolyte salt and an organic solvent, wherein the electrolyte solution further includes a compound represented by Chemical Formula 1 below as an additive:

[Chemical Formula 1]

wherein R is a linear or branched alkylene group with a carbon number of 1 to 3,
$R_1$ is a linear or branched alkylene group with a carbon number of 1 to 5 or arylene group with a carbon number of 5 to 8, and
when $R_1$ is a linear or branched alkylene group with a carbon number of 1 to 5, n is an integer of 1 to 10, and when $R_1$ is an arylene group with a carbon number of 5 to 8, n is an integer of 0 to 10.

2. The electrolyte solution of claim 1, wherein, in Chemical Formula 1, R is a linear alkylene group with a carbon number of 1 to 3, $R_1$ is an arylene group with a carbon number of 5 to 8, and n is an integer of 0 to 5.

3. The electrolyte solution of claim 1, wherein the compound represented by Chemical Formula 1 includes a compound of Chemical Formula 1a below or a compound of Chemical Formula 1b below.

[Chemical Formula 1a]

[Chemical Formula 1b]

4. The electrolyte solution of claim 1, wherein the compound represented by Chemical Formula 1 is included in an amount of 0.05 wt % to 7 wt % based on a total weight of the non-aqueous electrolyte solution.

5. The electrolyte solution of claim 4, wherein the compound represented by Chemical Formula 1 is included in an amount of 0.1 wt % to 5 wt % based on a total weight of the non-aqueous electrolyte solution.

6. The electrolyte solution of claim 1, wherein the electrolyte salt consists of a combination of (i) at least one positive ion selected from the group consisting of $Li^+$, $Na^+$, and $K^+$ and (ii) at least one negative ion selected from the group consisting of $PF_6^-$, $BF_4^-$, $Cl^-$, $Br^-$, $I^-$, $ClO_4^-$, $AsF_6^-$, $B_{10}Cl_{10}^-$, $CH_3CO_2^-$, $CF_3SO_3^-$, $CF_3SO_3^-$, $SbF_6^-$, $AlCl_4^-$, $AlO_4^-$, $CH_3SO_3^-$, $N(CF_3SO_2)_2^-$ and $C(CF_2SO_2)_3^-$.

7. The electrolyte solution of claim 6, wherein the electrolyte salt is any one or a mixture of two or more selected from the group consisting of LiCl, LiBr, LiI, $LiClO_4$, $LiBF_4$, $LiB_{10}Cl_{10}$, $LiPF_6$, $LiCF_3SO_3$, $LiCH_3CO_2$, $LiCF_3CO_2$, $LiAsF_6$, $LiSbF_6$, $LiAlCl_4$, $LiAlO_4$, $LiCH_3SO_3$, chloroborane lithium, lower aliphatic lithium carbonates, and lithium tetraphenylborate.

8. The electrolyte solution of claim 6, wherein the electrolyte salt further includes one or a mixture of two or more selected from the group consisting of lithium bisperfluoroethanesulfonimide ($LiN(C_2F_5SO_2)_2$, lithium fluoromethanesulfonimide, and lithium (bis)trifluoromethanesulfonimide ($LiN(CF_3SO_2)_2$).

9. The electrolyte solution of claim 1, wherein the electrolyte salt is included in a concentration of 0.8 M to 1.5 M.

10. The electrolyte solution of claim 1, wherein the non-aqueous organic solvent includes one solution selected from the group consisting of a cyclic carbonate solvent, a linear carbonate solvent, an ester solvent, and a ketone solvent or a mixed solution of two or more thereof.

11. A lithium secondary battery comprising a positive electrode, a negative electrode, a separator interposed between the positive electrode and the negative electrode, and a non-aqueous electrolyte solution,
 wherein the non-aqueous electrolyte solution is the non-aqueous electrolyte solution for a secondary battery described in claim 1.

* * * * *